United States Patent [19]

Franklin

[11] Patent Number: 4,471,154

[45] Date of Patent: Sep. 11, 1984

[54] STAGED, FLUIDIZED-BED DISTILLATION-REACTOR AND A PROCESS FOR USING SUCH REACTOR

[75] Inventor: Frederick C. Franklin, Pinole, Calif.

[73] Assignee: Chevron Research Company, San Francisco, Calif.

[21] Appl. No.: 503,087

[22] Filed: Jun. 10, 1983

[51] Int. Cl.³ .............................................. C07C 7/00
[52] U.S. Cl. ............................ 585/864; 203/DIG. 6; 422/140; 422/142; 422/193
[58] Field of Search ................ 585/864; 422/140, 142, 422/191, 311, 193, 195, 145, 141; 203/DIG. 6

[56] References Cited

U.S. PATENT DOCUMENTS

| 3,556,737 | 1/1971 | Boyd | 422/191 |
| 3,634,534 | 1/1972 | Haunschild | 585/864 |
| 3,652,450 | 3/1972 | Boyd | 422/191 |

| 4,194,964 | 3/1980 | Chen et al. | 288/59 |
| 4,295,967 | 10/1981 | Kurima et al. | 422/140 |

Primary Examiner—Delbert E. Gantz
Assistant Examiner—Anthony McFarlane
Attorney, Agent, or Firm—Burns, Doane, Swecker & Mathis

[57] ABSTRACT

A distillation-reactor for separating constituents of a feedstock having similar boiling points includes at least one stage with containing screens defining a series of containment volumes for a heterogeneous particulate catalyst. The catalyst is fluidized within the volumes defined by the containing screens by the action of vapor passing through the tray. Liquid flowing across the tray intimately contacts the fluidized catalyst and vapor without the occurrence of liquid back-up or high pressure drop.

12 Claims, 3 Drawing Figures

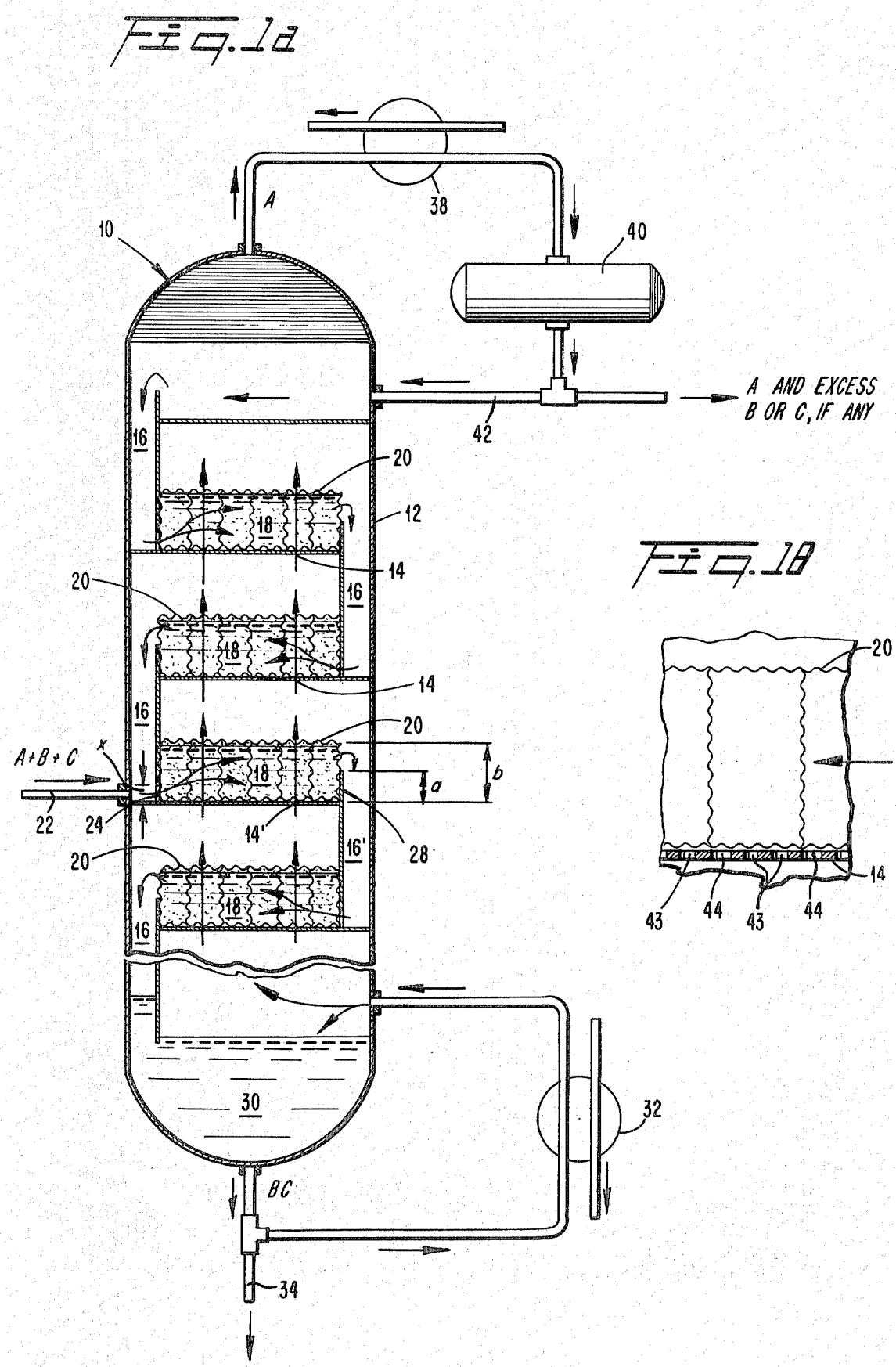

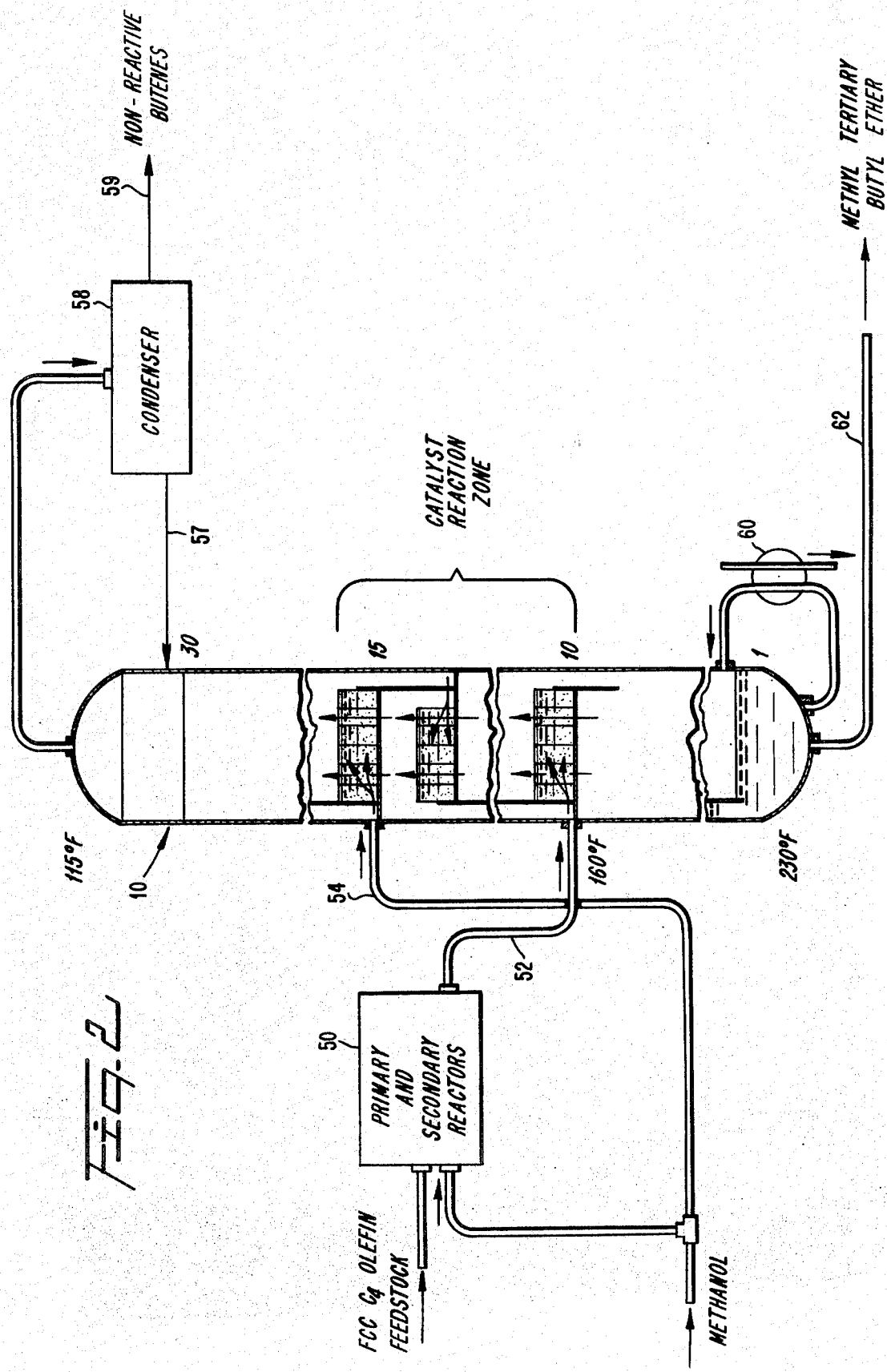

STAGED, FLUIDIZED-BED DISTILLATION-REACTOR AND A PROCESS FOR USING SUCH REACTOR

BACKGROUND OF THE INVENTION

1. Field of the Invention

The present invention relates to a staged, fluidized bed distillation reactor. Such a reactor may be used for simultaneously performing distillation and heterogeneous catalysis to separate reactants from the product of the catalytic reaction. In a further aspect, the present invention relates to process for catalytically reacting and separating materials in a novel fluidized bed distillation reactor.

2. Description of the Prior Art

The reaction and separation of materials in a distillation reactor is generally known in the art. For example, the reaction of a stream of mixed olefins with methanol to form an ether which is removed from the remaining olefin stream in a distillation reactor is disclosed in U.S. Pat. Nos. 3,629,478, 3,634,534 and 3,634,535 to Haunschild. In the process of U.S. Pat. No. 3,629,478, a mixture of tertiary pentenes and linear pentenes is fed to a distillation column reactor. An alcohol is also fed to the reactor. The mixture of pentenes and alcohol is contacted with a heterogeneous catalyst in the reactor downcomers, to thereby catalytically react the tertiary pentene with the alcohol to form an ether. The ether is then fractionated from the linear pentenes in the reactor.

As explained in the '478 patent, the reaction of tertiary olefins with alcohols having 6 or less carbon atoms is equilibrium limited. This equilibrium limitation is overcome in the prior art by carrying out the reaction in a distillation reactor. When the ether is formed in the distillation reactor, it is relatively easy to fractionate the ether away from the olefins. In the distillation reactor the heavier or less volatile component, e.g., the ether, is constantly fractionated away from the reaction zone and the reaction does not reach equilibrium.

Although such prior art systems operate successfully, it is preferable that processes be undertaken in a vessel which has a relatively small volume, yet still provides the required catalyst volume and the vapor-liquid capacity required for distillation. In addition, the system should avoid bypassing of the vapor or liquid so that neither the catalytic reaction nor the vapor-liquid mass transfer efficiency is jeopardized.

Typically, the catalyst used in heterogeneous catalysis must be particulate to assure efficient reaction. However, beds of such small sized particulates make poor distillation column packing due to their low vapor capacity and high pressure drops across such beds. As noted above, the distillation reactors shown in the Haunschild patents employ beds of catalyst in the reactor downcomers. While this arrangement permits the process to be performed, the practical design of downcomers to convey liquid through the catalyst with the limited liquid head available can result in very inefficient use of the space within the distillation reactor.

A further example of a distillation reactor is set forth in U.S. Pat. Nos. 4,194,964 and 4,213,847 to Chen et al. In these patents, heavy petroliferous stocks are concurrently distilled and hydroprocessed for removal of sulfur, nitrogen and metals and are hydrocracked or otherwise hydroprocessed in a packed distillation column under hydrogen pressure.

In U.S. Pat. No. 3,506,408 to Kageyama et al, a multistage reaction apparatus is shown. The apparatus comprises a liquid feed inlet at the top of the apparatus, a gas inlet at the bottom of the apparatus and a plurality of perforated trays containing catalyst beds. The liquid passes downward through the catalyst on the trays and the gas zig-zags around the trays such that there is essentially no counter-current contact of liquid and gas within the catalyst beds, and very inefficient fractionation of vapor and liquid components in the desired manner.

It has been proposed in U.S. Pat. No. 4,215,011 to Smith, Jr., to contain particulate catalyst in an array of closed cloth pockets supported by wire mesh in a reaction-distillation column. Such an array has the disadvantage of being relatively difficult and expensive to construct and replace. Also, such a catalyst system would require restructuring of conventional distillation columns. Finally, the catalyst dispersion could not be uniform throughout the array, but rather is concentrated in the pockets. Therefore, very inefficient contacting of liquid and vapor with the catalyst will result causing very poor utilization of catalyst to achieve the desired chemical conversion.

Accordingly, it is an object of the present invention to provide, in the limited volume of a conventional distillation reactor, structures employing a particulate catalyst bed with high liquid and vapor capacity and low pressure drop.

It is another object of the present invention to provide an easily fabricated catalyst packing for a conventional distillation reactor.

It is another object of the present invention to provide a distillation reactor, with vapor and liquid flows facilitating high heterogenous catalytic reaction rates and mass transfer efficiency by providing intimate mixing of catalyst with the liquid and vapor.

It is a further object of the present invention to provide a process for reacting and separating material from a feedstream in a novel distillation reactor.

It is a still further object of the present invention to provide an improved process for separating non-tertiary olefins from tertiary olefins.

These and other objects and features of the invention will become apparent from the claims, and from the following description when read in conjunction with the accompanying drawings.

SUMMARY OF THE INVENTION

According to the present invention, a staged, fluidized bed distillation reactor is provided including a reactor vessel containing a plurality of trays vertically spaced from one another. The trays are interconnected by downcomers for conducting liquid downward from tray to tray. At least some trays may each carry a quantity of heterogeneous particulate catalyst. The particulate catalyst is retained by containing screens above each tray in such a way that the bed may expand or fluidize in response to the passage of distillation vapor through the tray. At the same time, the fluidized bed allows adequate space for liquid cross flow between downcomers feeding successive trays in the reactor. In this way the average bed void fraction is maximized so that minimum equipment volume is required to handle the liquid and vapor flows. In addition, minimum bypassing of the bed of the catalyst occurs because the liquid preferentially flows horizontally through the fluidized bed as the vapor passes vertically through the tray and the bed.

Ordinarily, a modified sieve-type distillation tray may be employed in practicing the invention. Hence, the distillation reactor of the present invention may be constructed using available parts or an existing distillation column can be readily converted. Containing screens for each tray may occupy most of the space between the trays and substantially all of the bubbling area between the downcomer discharging liquid onto the tray and the liquid outlet from the tray. The containing screens allow for expansion of the bed during operation. In other words, the particulate catalyst is entrained in rising vapors in the vessel whereby the catalyst is fluidized within a volume defined by the trays and their respective containing screens.

In a preferred embodiment of the present invention, the quantity and size of the catalyst, the size and configuration of each tray and its respective containing screens and vapor flow through the tray are selected so that the height of the catalyst fluidized above each tray ranges from about 1.1 to about 10.0 times, and preferably from about 2.0 to about 5.0 times the settled height of the catalyst on said tray.

In another preferred embodiment of the present invention each tray has at least one entry port from a downcomer through which liquid from the downcomer passes to the tray. Opposite the entry port, an overflow weir may be provided over which liquid from the tray passes to another downcomer whereby a liquid level is maintained on the tray. The height of the overflow weir may be selected to be approximately equal to the height of the settled bed of particulate catalyst and typically is sufficient to provide a liquid seal at the downcomer inlet.

In another preferred embodiment of the present invention, the containing screens are spaced at about 3 to 18 inch intervals and preferably at about 6 to 12 inch intervals perpendicular to the direction of liquid flow and extend upward from at or near the overflow weir to at or near the liquid inlet, and horizontally over the tray to provide a series of contiguous containment volumes across the tray. The horizontal segment of the containing screen is at a height of about 25 to 100% and preferably 50 to 90% of the tray spacing. A bottom horizontal containing screen is also located on the tray deck to retain catalyst during times when there is no vapor flow through the tray, for example during a shut down of the operation. The catalyst is advantageously distributed equally in the contiguous containment volumes of a given tray.

In another preferred embodiment of the present invention, a sieve-type tray is modified to provide slots for a portion of the vapor flow through the tray at points immediately upstream of each vertical screen, with respect to the liquid flow direction, so as to sweep catalyst off the vertical containing screen and continually remix this catalyst into the flowing liquid by means of the agitation obtained by this vapor stream flow. The remaining sections of the tray may contain holes like a sieve tray, or none, as required by the vapor flow rate to achieve the desired degree of fluidization.

Such a distillation reactor may be provided for receiving a feedstock including multiple hydrocarbon constituents having similar boiling points, the object being to separate these constituents. A reactive substance may be added to the multiple hydrocarbon constituents either before or after entry into the distillation reactor. The reactive substance selectively engages in an equilibrium limited reaction with at least one of the hydrocarbon constituents in the presence of the catalyst to form a reaction product having a boiling point sufficiently different from remaining feedstock constituents to permit separation by distillation. The reactor permits the establishment of countercurrent flow of downflowing liquid materials and upward flowing gaseous materials. In a preferred embodiment, the feedstock includes a tertiary olefin and the reactant may be an alcohol.

BRIEF DESCRIPTION OF THE DRAWINGS

FIGURE 1A is a schematic diagram of a staged, fluidized bed distillation reactor, constructed according to a preferred body of the present invention.

FIGURE 1B is an enlarged view of one full containment volume and a portion of the contiguous containment volumes.

FIG. 2 is a schematic diagram of a system for separating tertiary and non-tertiary butenes employing a distillation reactor such as that shown in FIG. 1.

DETAILED DESCRIPTION OF THE INVENTION

Referring first to FIGURE 1A, a staged, fluidized bed distillation reactor is indicated generally by the numeral 10. The reactor 10 includes a vessel 12 and a plurality of vertically spaced, modified sieve-type distillation trays 14. The spacing between the trays varies depending on several factors, such as the other dimensions of the reactor and the amount and nature of the feedstock. In general, the trays may be spaced by from about 10 to about 40 inches, more typically from about 18 to about 30 inches.

A downward flowing liquid flow path is provided between the trays by downcomers 16. A particulate catalyst (shown in the fluidized state) is located on the trays in the regions 18 shown as shaded areas in FIGURE 1A. The catalyst may be of various shapes, such as spheres or cylinders and may have an average particle size in the range of from about 0.01 to about 0.25 inches preferably from about 0.02 to about 0.1 inches. Catalysts which may be used in the present invention include ion exchange resin type catalysts such as Amberlyst 15 available from Rohm and Haas Company. A containment volume is defined above each tray by a containing screen 20 which is constructed of a material, such as stainless steel, which will effectively contain the catalyst and which will not be adversely affected by the reactor conditions. Of course, if further separation of the streams is desired, the reactor may contain further conventional sieve trays, which do not include catalyst, at either the top or bottom of the reactor.

The bed heights of the particulate catalyst on one of the trays 14' is indicated schematically in FIGURE 1A. The settled height of the catalyst bed is indicated by the letter a and is preferably substantially the same in all containment volumes of a particular tray. A fluidized height, i.e., the height of the bed when the catalyst is entrained in upward gaseous flow, is indicated by the letter b. It will be understood that the fluidized height of the bed is determined, at least in part, by the volume defined by the tray 14' and the containing screen 20. Generally, the height defined by the containing screen ranges from about 2 to about 10 times and preferably from about 5 to about 10 times the height of the settled catalyst bed. The height of the containing screen is of course limited by the spacing of trays. Typically, the height of the containing screen ranges from about 25% to about 100% of the tray spacing and more preferably from about 50% to about 90% of the tray spacing.

As stated previously, the vertical sections of the containing screen 20 are spaced at intervals ranging from about 3 to about 18 inches, preferably from about 6 to about 12 inches. With reference to FIG. 1B, an individual containment volume is defined by containing screen 20 at the top to prevent catalyst loss, at the sides to prevent excessive catalyst shifting and at the bottom to prevent catalyst fall-through during periods of reduced or no vapor flow (e.g., shutdown). The ends of the containment are generally defined by the walls of vessel 10 (not shown).

Below the bottom containing screen is tray 14. The tray is preferably designed to promote agitation and fluidization of the catalyst. This is accomplished by permitting a larger portion of vapor flow to pass through tray 14 adjacent the upstream side of the containing screen. As shown in FIG. 1B, the flow of liquid across tray 14 is from right to left as indicated by the arrow. In contrast to openings 43, openings 44 are larger and therefore permit a larger proportion of the vapor to flow upward adjacent to the upstream side of the containing screens. This increased vapor flow counteracts the tendency of the liquid flow to push the catalyst against the containing screen and therefore promotes agitation, fluidization and improved contact of the constituents with the catalyst. By the same token, the tendency of channeling and liquid back-up to occur is greatly reduced.

Openings 44 can be formed in a conventional sieve tray by drilling a larger number of holes or a series of larger holes in the appropriate locations or, more preferably, by forming a slot adjacent and parallel to the upstream side of the containing screen such that the vapor sweeps over substantially all of the downstream screen. In this latter regard, the tray may have supports bridging the slots as required to maintain the structural integrity of tray 14 and/or may have means to adjust the width of the slots.

The operation of the distillation reactor will now be described. Advantageously, a feedstock may be introduced into the reaction zone of the distillation reactor as indicated by the arrow 22. The feedstock may contain a mixture of constituent liquid materials having nearly the same boiling point. For simplicity's sake, these hypothetical materials will be identified as a two part system consisting of chemical A and chemical B, it being understood that more than two constituent materials may be contained in the feedstock. Typically, A and B will have very similar boiling points, otherwise A and B could be separated by normal distillation techniques. Thus, the molecules of A and B will be of very similar size. A third hypothetical material, C, may be mixed with the feedstock materials A and B before introduction into the distillation reactor or may be independently introduced at a different level in the distillation reactor. The material C is a material which will preferentially react with at least one of the constituents of the feedstock in the presence of the catalyst. Normally, the boiling point of C will be similar to, but preferably higher than, those of A and B.

The reaction is limited by equilibrium and forms a product having a boiling point which will obviously be higher than the remaining constituents of the feedstock because it has a larger molecule than A, B or C, as defined. Assuming that C preferentially reacts with B under the reaction conditions, generalized equilibrium reaction is indicated by the following formula:

$$A+B+C \rightleftarrows A+BC.$$

It should be apparent to those of ordinary skill in the art that other reactions can be conducted in the distillation reactor of the present invention. For example, a decomposition reaction, such as that disclosed in U.S. Pat. No. 3,634,534, may also be successfully conducted in the distillation reactor.

In operation the feedstock material is introduced into one of the trays such as 14' through an inlet port 24. The liquid will generally flow through catalyst above the tray in the manner indicated by the arrows 26. Liquid reaching the opposite side of the tray will flow over the weir 28 and into the downcomer 16', by which it enters a subsequent lower level tray in the distillation reactor. Ultimately, the liquid reaches a reservoir 30 in the bottom of the distillation reactor. In accordance with the principles of distillation which are in operation, the material reaching the bottom of the distillation reactor will be the constituent having the highest boiling point, i.e., the compound BC. Some of this material will be circulated through a reboiler 32 to vaporize a portion of the material according to standard distillation practice, and returned to the bottom of the distillation reactor. The remainder of the compound BC is tapped from the distillation reactor as indicated by the arrow 34.

With continuing reference to the generalized chemical reaction discussed above, the materials A and unreacted B and C will be preferentially vaporized into the rising vapor in the distillation reactor. The vapor will rise through the catalyst bed as indicated by the arrows 36. This rising vapor will tend to fluidize the catalyst as it passes through the reactor thereby enhancing the reactive properties of the system by exposing more reactive surfaces and reducing impairment of liquid flow through the bed. The flows of vapor and/or liquid can be selected such that the height of the fluidized catalyst ranges from about 1.1 to about 10 times, preferably from about 2.0 to about 5.0 times the settled height of the catalyst.

B and C will continue to react and be removed from the rising vapors with BC being rejected to the bottom of the distillation reactor. As BC is thus removed, equilibrium will no longer limit the reaction of B and C so that eventually all of B or C (or both depending on their ratio in the feed) will be converted and removed from the rising vapor. Thus, only A and the excess of B or C, if any, will arrive at the top of the distillation reactor. Normally, C would be added in an amount to at least consume all of B so that normally no B would be in the distillate with A. The excess of C, if any, could then be separated from A in a subsequent step and recycled to the distillation reactor.

The material A and the excess of B or C, if any, may be removed as a vapor from the top of the distillation reactor and passed through an overhead condenser 38. The condensed liquid may be collected in a reflux drum 40. A portion of the collected liquid may be directed to further processing steps and a portion returned to the distillation reactor as reflux, indicated by the arrow 42. By this mechanism countercurrent vapor and liquid flow is established within the distillation reactor and particularly within the catalyst beds.

By using the distillation reactor of the present invention, the processes described in the aforementioned U.S. Patents to Haunschild and Chen et al, the contents of which are incorporated by reference, and other processes wherein distillation reactors are suitable may be successfully conducted to obtain high yields in a smaller reactor volume. Thus, for example, the present distillation reactor may be used to react preferentially a tertiary olefin with an alcohol.

FIG. 2 is a schematic diagram of an exemplary system for separating tertiary and non-tertiary (i.e., linear) butenes employing a distillation reactor such as that described in connection with FIG. 1A. In the system, a feedstock identified as "FCC-$C_4$ olefin feedstock" is provided to primary and secondary reactors 50 which are of a conventional variety. The FCC-$C_4$ olefin feedstock contains both tertiary and non-tertiary butenes. Typically, the feedstock contains from about 8 to about 20 mole percent of isobutene and an exemplary feedstock may contain 14 mole percent isobutene.

Methanol is also provided to the primary and secondary reactors 50 advantageously at a mole ratio of 1.5:1 (moles of methanol to mole of isobutene). The temperature of this mixture entering the primary and secondary reactors (50) will advantageously be at about 125° F. and at about 220 psig to ensure that only a liquid phase exists in the reactors (50). These reactors yield a product in which the tertiary butene has undergone about a 91% conversion to methyl tertiary butyl ether. This product of the primary and secondary reactors, is fed via conduit 52 at a temperature of about 160° F., to the catalyst reaction zone of the distillation reactor 10. Additional methanol may be added to a higher stage of the distillation reactor via conduit 54.

The distillation reactor is operated generally in the manner described in connection with FIG. 1A. Depending on several factors, the reactor may have about 30 trays, about 5 of which have catalyst thereon. This leaves about 15 distillation trays above the reaction zone and about 10 distillation trays below the reaction zone. The catalyst on the trays is Amberlyst 15, having an approximately spherical shape and an average particle size of 0.029 inches. The settled height of the catalyst bed is 4 inches and the contained height is about 18 inches.

The temperature gradient from top to bottom of the distillation reactor is indicated in FIG. 2 as ranging from about 230° F. at the bottom of the vessel to about 115° F. at the top of the vessel. The top of the distillation reactor is maintained at about 60 psig and the overhead vapor is withdrawn via conduit 56. The overhead vapor contains non-tertiary olefins and paraffins which are further processed by a condenser 58. A portion of the condensed vapor is returned to the distillation reactor as reflux via line 57, in accordance with standard distillation practice. The remaining condensate containing non-tertiary (i.e., linear) butenes is withdrawn from the condenser may be directed to further processing, for example by alkylation, via line 59.

The liquid fraction which collects at the bottom of the distillation reactor may be recirculated through reboiler 60 and heated by the introduction of steam into the reboiler. The reboiler and condenser, in the distillation reactor are operated such that sufficient vapor passes through the trays to fluidize the catalyst bed thereon and provide vapor required to remove the non-reactive components of the feed 52 by standard fraction techniques. In the embodiment shown in FIG. 2, fluidization requires a superficial velocity in the range of from about 5 to about 20 ft./sec., based on the open area through the tray for vapor flow. Of course, these values will vary with process conditions, tray design and system properties.

Typically, liquid material withdrawn from the bottom of the distillation reactor via conduit 62 is 99.5% reacted. Essentially 100% of the reaction product in the material withdrawn is methyl tertiary butyl ether. The remaining portion is unreacted methanol. This material may be further processed to recover methanol to recycle it to the reactor system and to purify the product, if desired.

Modifications of the above-described embodiments of the invention that are obvious to those of ordinary skill in the refining, chemical processing, and related arts are intended to be within the scope of the following claims.

What is claimed is:

1. A process for catalytically reacting at least one component from a feedstream and separating resulting materials having different boiling points comprising:
    (a) introducing the feedstream into a distillation reactor which includes a plurality of trays vertically spaced from one another and interconnected by downcomers for conducting liquid downward from tray to tray, at least some of said trays further containing a quantity of particulate catalyst located thereon, the upward and sideward movement of said particulate catalyst being confined by containing screens which define a series of containment volumes associated with each of the particulate catalyst containing trays;
    (b) operating the distillation reactor such that (1) a stream of vapor passes upward through the trays thereby fluidizing any particulate catalyst thereon and (2) a stream of liquid passes downward through the downcomers, across the trays into contact with the upward passing vapor and, on these trays containing the catalyst, through the containing screens and into contact with the fluidized particulate catalyst, thereby causing a catalytic reaction to occur;
    (c) removing a lower boiling material from the upper portion of the distillation reactor; and
    (d) removing a higher boiling material from the lower portion of the distillation reactor.

2. The process of claim 1 wherein the feedstream contains at least two components having nearly the same boiling point and a material which preferentially reacts with one of components in the presence of the particulate catalyst and which is also introduced into the distillation reactor.

3. The process of claim 2 wherein the reacting material is introduced to the distillation reactor separately from the component with which it is to be reacted.

4. The process of claim 2 wherein the height of the fluidized particulate catalyst is from about 1.1 to about 10 times the settled height of the particulate catalyst.

5. The process of claim 1 wherein the feedstream contains a component which is decomposed in the presence of the particulate catalyst in accordance with an equilibrium limited reaction.

6. A process for treating a feedstock comprising at least one non-tertiary olefin and at least one tertiary olefin comprising:
    (a) introducing the feedstock into a distillation reactor which includes a plurality of trays vertically spaced from one another and interconnected by downcomers for conducting liquid downward from tray to tray, at least come of said trays further containing a quantity of particulate catalyst located thereon, the upward and sideward movement of said particulate catalyst being confined by containing screens which define a series of containment volumes associated with each of the particulate catalyst containing trays;

(b) introducing an alcohol to the distillation reactor;

(c) contacting a mixture of the tertiary olefin and the alcohol with the particulate catalyst wherein a stream of vapor passing upward through the trays fluidized any particulate catalyst contained thereon and wherein a liquid stream flowing downward through the downcomers, across the trays into contact with the upward passing vapor and, on those trays containing the catalyst, through the containing screens and into contact with the fluidized particulate catalyst thereby catalyzing the reaction of the tertiary olefine and the alcohol to form an ether;

(d) fractionating the either from the non-tertiary olefins in the distillation reactor;

(e) withdrawing a stream rich in the either from the lower portion of the distillation reactor; and (f) withdrawing a stream rich in the non-tertiary olefine from the upper portion of the distillation reactor.

7. The process of claim 6 wherein the alcohol is methanol.

8. The process of claim 7 wherein the feedstock includes non-tertiary butenes and isobutene.

9. The process of claim 8 wherein the catalyst has an average particle size in the range of from about 0.01 to about 0.05 inches.

10. The process of claim 8 wherein the temperature in the distillation reactor ranges from about 115° F. to about 230° F.

11. The process of claim 6 wherein the height of the fluidized particulate catalyst is from about 1.1 to about 10 times the settled height of the particulate catalyst.

12. The process of claim 6 wherein the height of the fluidized particulate catalyst is from about 2.0 to about 5.0 times the settled height of the particulate catalyst.

* * * * *

UNITED STATES PATENT AND TRADEMARK OFFICE
CERTIFICATE OF CORRECTION

PATENT NO. : 4,471,154
DATED : September 11, 1984
INVENTOR(S) : Frederick C. Franklin It is certified that error appears in the above-identified patent and that said Letters Patent is hereby corrected as shown below:

In claim 6, column 9, line 2, amend "come" to --some--;

line 13, amend "fluidized" to --fluidizes--;

line 20, amend "olefine" to --olefin--;

column 10, line 1, amend "either" to --ether--;

line 3, amend "either" to --ether--;

lines 5 and 6, amend "olefine" to --olefin--.

Signed and Sealed this

Nineteenth Day of February 1985

[SEAL]

Attest:

DONALD J. QUIGG

Attesting Officer    Acting Commissioner of Patents and Trademarks